(12) United States Patent
Woods et al.

(10) Patent No.: US 6,355,817 B1
(45) Date of Patent: Mar. 12, 2002

(54) OPTIMIZED CATALYST ADDITION TO ENHANCE ESTERIFICATION CATALYST PERFORMANCE

(75) Inventors: David G. Woods; Larry O. Jones, both of Baton Rouge, LA (US); Pei-Yi Lo, Pittsburgh, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/616,329

(22) Filed: Jul. 15, 2000

(51) Int. Cl.[7] .................................. C11C 3/00
(52) U.S. Cl. ................. 554/170; 562/210; 562/215
(58) Field of Search ................ 554/170; 502/210, 502/215

(56) References Cited

U.S. PATENT DOCUMENTS

| | | | |
|---|---|---|---|
| 3,056,818 A | 10/1962 | Werber | 260/410.6 |
| 4,795,824 A | 1/1989 | Kippax et al. | 560/204 |
| 5,349,075 A | 9/1994 | van den Berg et al. | 554/170 |

FOREIGN PATENT DOCUMENTS

| | | | | |
|---|---|---|---|---|
| GB | 1426057 | | 2/1976 | C07C/69/76 |
| GB | 2314081 | * | 12/1997 | C07C/67/08 |
| WO | 99/28033 | * | 6/1999 | C07C/67/08 |

OTHER PUBLICATIONS

Vol. 9 of the *Kirk–Othmer Encyclopedia of Chemical Technology*, Fourth Edition (1994), pp. 762–768.
Russian language journal Khim. Prom–st., Ser.: Proizvod. Pererab. Plastmass Sint. Smol (1981), (8), pp. 19–21.
D. C. Bradley et al., *Metal Alkoxides*, (1978), pp. 150–166.
Vol. A20 of *Ullman's Encyclopedia of Industrial Chemistry*, Fifth Edition (1992) pp. 193–196.
Vol. 9 of the *Kirk–Othmer Encyclopedia of Chemical Technology*, Fourth Edition (1994), pp. 764–767.

* cited by examiner

*Primary Examiner*—Deborah D. Carr
(74) *Attorney, Agent, or Firm*—Douglas J. Collins

(57) ABSTRACT

The present invention provides a process for the production of an ester, including reacting an alcohol with a carbonyl-like compound in the presence of a first esterification catalyst; and adding a second esterification catalyst to the reaction mixture at some time after initiation of the esterification reaction. The staged addition of the esterification catalyst according to the present invention provides a reduced reaction time to achieve a targeted conversion to esters.

42 Claims, No Drawings

OPTIMIZED CATALYST ADDITION TO ENHANCE ESTERIFICATION CATALYST PERFORMANCE

FIELD OF THE INVENTION

The present invention relates to the catalyzed production of esters primarily from alcohols and carboxylic acids or anhydrides. More particularly, the present invention is directed to an improved process for preparing plasticizer esters for polyvinylchloride (PVC) such as phthalates, adipates and trimellitates in the presence of a titanium, zirconium, or tin-based organometallic catalyst. The current invention is also useful for preparing polyol esters.

BACKGROUND OF THE INVENTION

Esters are most commonly prepared by the reaction of a carboxylic acid and an alcohol accompanied by the elimination of water. Esters may also be formed by reaction of an alcohol with various other reactants including acid anhydrides, acid chlorides, amides, nitrites, ethers, aldehydes, and ketones.

The reaction conditions under which esterification is effected can be varied considerably. The reaction proceeds very slowly at room temperature, but quite rapidly at elevated temperatures. About 99% of the limiting reagent, e.g., acids, anhydrides, or polyols, can be converted to an ester within a few hours. Limiting reagents are typically reagents which are not present in stoichiometric excess, e.g., limiting reagents used to make plasticizers include diacids and phthalic anhydride and those used to make polyol esters are polyols.

Because the esterification of an alcohol and an organic acid or anhydride is a reversible reaction, the esterification reaction normally does not go to completion. However, conversions of over 99% can be achieved by removing at least one of the esterification products, typically water, by distillation. A variety of distillation techniques are known in the art to remove the produced water from the reaction zone. One method of water removal includes carrying out the reaction in a liquid medium which may form an azeotrope having a boiling point that is lower than that of either component of the reaction. If the resulting ester has a boiling point well above 100° C. at atmospheric pressure, then the reaction temperature can be adjusted such that no liquid medium capable of forming an azeotrope is required. Additionally, an entrainer may be used to aid in the distillation of the water from the reaction mixture. Inert materials such as benzene, toluene, or xylene may be used as an entrainer in the production of phthalate esters. In addition, the reactant having the lower boiling point has also been employed as the entrainer. In this latter case, the reactant used as the entrainer is charged into the reaction mixture in excess over the stoichiometric quantities required for the reaction. Esterification processes, including those employing water removal, may be conducted in a batch or continuous mode of operation. Various esterification processes are disclosed in Volume 9 of the *Kirk-Othmer Encyclopedia of Chemical Technology*, Fourth Edition (1994), pp. 762–768, the entirety of which is hereby incorporated by reference.

The batch esterification procedure includes charging all of the reactants into the reactor at the beginning of the reaction cycle. In catalytic esterification processes, the catalyst is typically added to the reaction mixture at the beginning of the reaction cycle after reaching a target temperature. The reaction mixture is then heated and reaction begins. The temperature of the reaction mixture rises until the boiling point of the reaction mixture is achieved, at which point the entrainer, if used, and water by-product boil out of the reaction mixture. Typically, the overhead vapors are condensed, the water separated from the entrainer, and the entrainer recycled to the reactor vessel. The reaction temperature, and, therefore, the rate of reaction, is partially determined by the boiling point of the reaction mixture. When the reactant with the lower boiling point is also used as the entrainer, its concentration is gradually reduced as the reaction proceeds. Thus the reaction temperature, and, therefore, the rate constant for the reaction, increases as the reaction proceeds.

One conventional process for forming plasticizer esters is disclosed in Great Britain Patent Specification No. 1,426,057 (Imperial Chemical Industries Limited), wherein plasticizer esters are prepared from phthalic anhydride and a $C_4$ to $C_{14}$ alkanol or mixture of such alkanols. For example, a mixture of phthalic anhydride and one or more of these alkanols may be heated gradually up to 180° to 260° C. in the presence of a titanium catalyst (e.g., titanium isopropoxide). When the temperature reaches 180° to 260° C., the esterification is substantially complete although the residual acidity is about 0.3 to 0.05 mg KOH/gram. Aqueous sodium carbonate solution is then slowly added to the ester product to provide 1 to 12 times the stoichiometric amount of alkali. When the temperature has fallen to 150° to 200° C. water or a dilute aqueous alkali solution is admitted and the excess alkanol is removed. By this treatment, the titanium catalyst is converted to titanium oxide and precipitated, and, thereafter, may be filtered off with excess sodium carbonate and the residual acidity is reduced to less than 0.05 mg KOH/gram.

Conventional esterification processes may be accomplished in two reaction steps. The first reaction step generally occurs in the absence of an esterification catalyst, while the second reaction step may include the use of an esterification catalyst. In U.S. Pat. No. 5,349,075 to van den Berg et al. a two step esterification process with a first uncatalyzed esterification reaction step conducted at a temperature of at least 200° C., followed by a catalyzed second esterification reaction step at a temperature below 100° C. is proposed. The process employs a solid acid catalyst in the second reaction step.

U.S. Pat. No. 4,795,824 to Kippax et al. proposes a two-step esterification process for the production of dialkyl maleate by reaction of maleic anhydride with an alkyl alcohol. In the first step, maleic anhydride is reacted with an alkyl alcohol to form a monoester in the absence of a catalyst. The second esterification reaction step reacts the monoester with alkyl alcohol in the presence of an esterification catalyst to form the di-ester.

In the Russian language journal Khim. Prom-st., Ser.: Proizvod. Pererab. Plastmass Sint. Smol (1981), (8), pages 19–21, di (2-ethylhexyl) phthalate production was reportedly investigated at temperature ranges from 170°–190° C., catalyst concentrations from 0 to 2.5% of the weight of phthalic anhydride, excess alcohol from 10 to 100%, and a vacuum in the range of 350–500 mm Hg (54.7–34.7 kPa). The reference concludes that the catalyst activity is almost two times higher when added at 180° C. as compared to 165° C. The reference proposes that it is best to conduct the esterification reaction in two stages to a depth of conversion of 60–70% without catalyst and then to add esterification catalyst (tetrabutoxytitanium) after the reaction conversion is 60–70%.

In the commercial production of plasticizer esters, e.g., phthalates, adipates, and trimellitates, conversions of greater than 99% are desired. For polyol esters, e.g., esters made from aliphatic acids and trimethyolpropane (i.e., the limiting reagent), the commercially desirable conversions are at greater than 98%. Typical product applications require conversions of about 98.5% of the original number of hydroxyl groups in the poly alcohol.

Most esterification processes are capable of converting about 99% of the limiting reagent, such as acids, anhydrides or polyols, to an ester within a few hours; however, after about 90% of the limiting reagent is converted, the rate of reaction tends to slow down substantially. It may take half as long again to convert the remaining 4–5% of limiting reagent as it took to convert the initial 95% thereof Since the chemical industry is continuously seeking to increase the rate of reaction, as well as the quality of the resultant esters, it would be quite desirable to develop a process which increases the overall rate of reaction, especially during the esterification of the last 10% of limiting reagent.

SUMMARY OF THE INVENTION

The present invention provides a process for the production of an ester. The process comprises: (a) reacting an alcohol with a carbonyl-like compound in the presence of a first amount of a first esterification catalyst; and (b) adding a second amount of a second esterification catalyst to the reaction mixture at some time after initiation of step (a). The second esterification catalyst may be the same or different from the first esterification catalyst.

The staged addition of the esterification catalyst according to the present invention provides a reduced reaction time to achieve a targeted conversion to esters. Additionally, the present invention may reduce or eliminate the haze which sometimes accompanies catalyzed ester production.

In another aspect, the invention provides a process for the production of an ester. The process comprises: (a) reacting an alcohol with a carbonyl-like compound in the presence of a first amount of a first esterification catalyst to form a reaction mixture, wherein said reaction mixture contains a cation species; and (b) adding a second amount of a second esterification catalyst to the reaction mixture at some time after initiation of step (a), wherein the second esterification catalyst is the same or different from the first esterification catalyst. The process thereby results in a shorter total reaction time as compared to a process where the entire amount of esterification catalyst is added at one time.

In addition to providing shorter esterification reaction run times and reduced haze formation as in the first-described aspect, this aspect of the invention also provides a process that more effectively handles a feed source which contains certain cationic catalyst poisons. In this aspect, it may be that the first catalyst addition also acts as sacrificial catalyst for the cationic poison. In this way, the first catalyst addition ties up the contaminant cationic species and results in a more active esterification catalyst mixture after the second stage catalyst addition.

In another aspect, the invention provides a continuous process for the production of an ester. The process comprises: (a) reacting an alcohol with a carbonyl-like compound in the presence of a first amount of a first esterification catalyst in a first reaction zone to form a first reaction product; and (b) reacting at least a portion of the first reaction product with a second amount of a second esterification catalyst in a second reaction zone to form a second reaction product, wherein the second esterification catalyst is the same or different from the first esterification catalyst.

The present invention also provides many additional advantages which shall become apparent from the following detailed description, examples, and appended claims.

DETAILED DESCRIPTION OF THE INVENTION

As used herein and in the claims, the term "carbonyl-like compound" refers to those organic compounds that are susceptible to forming an organic ester upon reaction with an organic alcohol under esterification conditions. Carbonyl-like compounds include anhydrides, carboxylic acids, acid chlorides, amides, nitrites, ethers, aldehydes, and keytones.

As used herein and in the claims, the term "ester" is used to refer to organic esters, including mono-esters, di-esters, tri-esters, and more generally multi-esters. The term "anhydride" is used to refer to organic anhydrides, including mono-anhydrides, di-anhydrides, and other multi-anhydrides. The term "carboxylic acid" is used to refer to mono-carboxylic acids, di-carboxylic acids, and other multi-carboxylic acids. The term "alcohol" is used to refer to any organic alcohol, including monohydric alcohols, dihydric alcohols, and polyhydric alcohols (polyols) generally.

Without limiting the invention scope, it is believed that the water produced by the esterification reaction has a detrimental effect upon the rate of conversion. For example, when an organo metallic catalyst (e.g., a titanium alkoxide catalyst) is employed in the esterification reaction, water is believed to hydrolyze and thus deactivate the catalyst. See, for example, D. C. Bradley et al., *Metal Alkoxides*, (1978), pp. 150–166, the entirety of which is hereby incorporated by reference. Additionally, it is thought that water contributes to haze formation in the esterification product when organo metallic esterification catalysts are used. Catalyst deactivation increases catalyst cost and esterification reaction run times. Esterification product haze formation raises product quality issues and can limit the marketability of the resulting esters in many applications. Therefore, it is desirable for an esterification process to have high conversion rates and for the ester product to be haze free.

The esters, according to the invention, are formed by the liquid phase reaction of a carbonyl-like compound and an alcohol. The preferred process for the esterification of acids or anhydrides, with at least one alcohol in accordance with the present invention, involves the addition of an acid or anhydride and at least one alcohol into a reaction vessel to form a reaction mixture. Preferably, plasticizer esters may be formed by reacting an anhydride with at least one alcohol. See Volume A20 of *Ullman's Encyclopedia of Industrial Chemistry*, Fifth Edition (1992) pp. 193–196, the entirety of which is hereby incorporated by reference. The process of the invention may be a batch or continuous process. Currently, a batch process is preferred. The reaction is preferably conducted by adding at least a stoichiometric amount of alcohol to the reaction zone. Preferably, the reaction is conduct ed using a 5 or 15 molar % excess of alcohol. More preferably, a 15 or 30 molar % excess of alcohol is used. This invention, while applicable to the catalyzed production of esters generally, is particularly applicable to the production of phthalates, adipates, and trimellitates. This general scheme is al so applicable to the production of polyol esters where the acid instead of the alcohol is preferably used in at lease stoichiometric amounts.

The pressure of the reaction vessel 1 should be maintained at a level sufficient to reflux the alcohol or acid (acting as an entrainer for water) and the water while forming an ester from the reactants. Typically, pressures ranging from a vacuum to low positive gauge pressure are used to carry out esterification reactions during the reaction cycle. The pressure of the reaction vessel is generally adjusted continually to ensure continuous vaporization and removal of water in the vapor. Typically, the initial reaction pressure is close to atmospheric pressure, for example 1 to 2 atm (101.3 to 202.6 kPa), and moves toward an increasing vacuum as the reaction proceeds. Preferably, the final reaction pressure ranges from 2 atm (202.6 kPa) to 100 mm Hg absolute (13.3 kPa). More preferably, the final reaction pressure ranges from 1.0 atm (101.3 kPa) to 200 mm Hg absolute (26.7 kPa). Most preferably, the final reaction pressure e ranges from 250 mm Hg absolute (33.3 kPa) to 350 mm Hg absolute (46.7 kPa).

Final reaction temperatures in esterification reactions are frequently determined by the boiling point of the reaction mixture. Initially, the esterification reaction is self-catalyzed by the acid reactant at temperatures from about 150°–190° C. Preferably, the self-catalyzed reaction occurs from about 160°–80° C. The first stage esterification catalyst addition takes place after the reaction mixture reaches about 160°–250° C. Preferably, the first stage catalyst addition occurs after the reaction mixture reaches about 170°–230° C. More preferably, the first stage catalyst addition occurs after the reaction mixture reaches about 175°–225° C. Most preferably, the first stage catalyst addition occurs after the reaction mixture reaches about 180°–220° C.

In the process of the current invention, it is desirable to add the second stage catalyst after the water concentration in the reaction zone is sufficiently low so as to not appreciably hydrolyze the second stage catalyst added. The second stage catalyst addition occurs after the residual water content is less than about 10,000 ppm based upon the total reaction mixture, not including the catalyst itself. Preferably, the second stage catalyst addition occurs after the reaction mixture contains less than about 5,000 ppm water. More preferably, the second stage catalyst addition occurs after the reaction mixture contains less than about 3,000; 2,000; or 1,000 ppm water. Most preferably, the second stage catalyst addition occurs after the reaction mixture contains less than about 800, 500, or 200 ppm water. Typically, although not necessarily, the second stage catalyst addition occurs after the reaction mixture reaches 200°–240° C.; however, the second stage catalyst addition is primarily related to the water concentration in the reaction mixture.

Without limiting the scope of the invention as claimed, it is theorized that the activity of certain esterification catalysts appears to be affected by the presence of certain cationic species within the reaction mixture. Cationic species, for example, $Li^{+1}$, $Na^{+1}$, $K^{+1}$, $Cu^{+1}$, $Rb^{+1}$, $Ag^{+1}$, $Cs^{+1}$, and $Au^{+1}$ can appear in the esterification reaction through a number of paths, including, for example, as a feed contaminant, a corrosion byproduct, or a catalyst impurity. It is believed that such species form ionic complexes with the catalyst and reduce the active catalytic sites on certain esterification catalysts, including, for example, titanium-containing catalysts. The staged catalyst addition of the current invention lessens the affect of cationic catalyst deactivation by providing sacrificial catalyst in the first catalyst addition step. The first catalyst addition ties up the cationic species and, thus, provides a more active catalyst for esterification reaction in the second catalyst addition stage.

The total amount of esterification catalyst used in the process of the current invention is determined primarily by four factors. First, the total reaction rate generally increases as the amount of catalyst, as represented as weight percent of catalyst per weight of sub-stoichiometric reactant (i.e., wt. % catalyst/anhydride), increases up to a certain optimal concentration, as determined by particular catalyst activity and the water content of the reaction mixture. Additionally, a relatively high concentration of catalyst may result in the organometallic complex esterification catalyst reacting with itself to form unreactive agglomerated catalyst. Second, a relatively higher concentration of certain esterification catalysts can cause product haze formation. Third, process economics dictate that beyond an optimal point, further catalyst addition is not economical. Fourth, if the reaction mixture contains an appreciable amount of certain cationic species, then the catalyst requirement must be increased to reach a desired reaction rate.

The total catalyst used in the process of the current invention, including all catalyst addition steps, to obtain optimal, economic esterification reaction rates is preferably from about 0.01 to 1.0 wt. % catalyst per weight limiting reactant. For reaction mixtures that contain less than 10 ppm of contaminant cationic species, more preferably, the total catalyst is from 0.10 to 0.45 wt. % catalyst per weight of limiting reactant. For reaction mixtures that contain less than 10 ppm of contaminant cationic species, most preferably, the total catalyst is from 0.15 to 0.30 wt. % catalyst per weight of limiting reactant. For reaction mixtures that contain greater than 10 ppm of contaminant cationic species, more preferably, the total catalyst is from 0.20 to 0.5 wt. % catalyst per weight of limiting reactant. For reaction mixtures that contain greater than 10 ppm of contaminant cationic species, most preferably, the total catalyst is from 0.25 to 0.45 wt. % catalyst per weight of limiting reactant.

Based upon the above-discussed total catalyst usage rates, the catalyst is added in two or more catalyst addition steps. Preferably, the catalyst is added in two catalyst addition steps. The current inventors have discovered that when too much catalyst is added in the first stage catalyst addition, the resulting esterification product may become hazy. Therefore, the first catalyst addition should contain enough catalyst to progress the reaction while not causing the esterification product to become hazy. The percentage of the total catalyst, which should be added in the first catalyst addition step, is from 5 to 80 wt. % of the total catalyst added in the esterification process. Preferably, 15 to 60 wt. % of the catalyst is added in the first catalyst addition step. More preferably, 35 to 55 wt. % of the total catalyst is added in the first catalyst addition step.

This process can also be used to convert polyols and acids to polyol esters. Polyols are organic alcohols, which contain two or more hydroxyl groups. The polyol ester process typically comprises the steps of esterification of the starting carbonyl-like compound with a polyol and a catalyst. In this instance the carbonyl-like compound, or mixture of carbonyl-like compounds, is added to the reaction mixture in stages such that it is present in an amount of at least about 5% of the stoichiometric requirements of the total of carbonyl-like compound required to react with the polyol. Preferably, a carboxylic acid is used as the carbonyl-like compound. Preferably, the carboxylic acid is added in 10°–40% stoichiometric excess. More preferably, the carboxylic acid is added in 15°–25% stoichiometric excess.

The esterification process may also include one or more of the following steps: removal of excess acid by nitrogen or steam stripping; addition of adsorbents such as alumina, silica gel, activated carbon, clay and/or filter aid to the reaction mixture following esterification before further treatment, but in certain cases adsorbent treatment may occur later in the process following steam stripping and in still other cases the adsorbent step may be eliminated from the process altogether; addition of water and base to simultaneously neutralize the residual organic acids and hydrolyze the catalyst (if present); filtration of solids from the ester mixture containing the bulk of the excess acid by steam or nitrogen stripping under vacuum and recycling of the acid to the reaction vessel; and, removing solids from the stripped ester in a final filtration.

The current invention may also be accomplished using a continuous process. In the continuous process, two or more reaction vessels or reaction zones are employed. Preferably, two to five reactors or reaction zones are employed. Each reactor vessel or zone contains a separate catalyst-to-feed contacting system. In this way, the feed to the continuous process is contacted with fresher catalyst in the second or later reactor vessels. The continuous, multi-stage reactor process should also achieve benefits similar to the batch process under conditions similar to those specified herein for the batch process. As an example of a benefit, for example, the continuous process may allow a target conversion to be achieved at a higher space velocity, thus resulting in higher total process feed rates. Examples of a continuous esterification process can be found in Volume 9 of the *Kirk-Othmer Encyclopedia of Chemical Technology*, Fourth Edition (1994), pp. 764–767, the entirety of which is hereby incorporated by reference.

The esterification process according to the present invention is conducted in the presence of an esterification catalyst. Esterification catalysts include acid catalysts and organometallic catalysts. Typical organometallic esterification catalysts include titanium, zirconium and tin catalysts such as titanium, zirconium and tin alkoxides, carboxylates and chelates. See U.S. Pat. No. 3,056,818 (Werber) which issued on Oct. 2, 1962, and which is incorporated herein by reference.

Typical titanium alkoxides which can be used as catalysts include tetramethyl titanates, tetraethyl titanates, tetrapropyl titanates, tetra-isopropyl titanates, tetrabutyl titanates, tetrapentyl titanates, tetrahexyl titanates, tetra-octyl titanates, tetranonyl titanates, tetradodecyl titanates, tetrahexadecyl titanates, tetra-octadecyl titanates, tetradecyl titanates, tetraheptyl titanates, tetraphenyl titanates, and mixtures thereof. The alkoxy groups on the titanium atom can all be the same or they can be different. The tin or zirconium counterparts of the above alcoholates can be substituted in whole or in part as catalysts.

The titanium carboxylates, which serve as esterification catalysts, are polymeric materials having at least one acyl group for each titanium atom. Typical titanium acylates which can be employed as catalysts include acylates from 2 to 18 carbon atoms, such as hydroxy titanium acetate, hydroxyl titanium butyrate, hydroxy titanium pentanoate, hydroxy titanium hexanoate, hydroxy titanium octanoate, hydroxy titanium decanoate, hydroxy titanium dodecanoate, hydroxy titanium tetradecanoate, hydroxy titanium hexadecanoate, hydroxy titanium octadecanoate, hydroxy titanium oleate, hydroxy titanium soya acylate, hydroxy titanium linseed acylate, hydroxy titanium castor acylate, hydroxy titanium tall oil acylate, hydroxy titanium coconut acylate, methoxy titanium acetate, ethoxy titanium butyrate, isopropoxy titanium pentanoate, butoxy titanium hexanoate, isopropoxy titanium octanoate, isopropoxy titanium decanoate, isopropyl titanium dodecanoate, isopropoxy titanium tetradecanoate, isopropoxy hexadecanoate, isopropoxy octadecanoate, isopropoxy titanium oleate, isopropoxy titanium soya acylate, isopropoxy linseed acylate, isopropoxy coconut acylate and mixtures thereof The alkoxy group of the acylate can vary from 1 to 20 carbon atoms. The corresponding tin and zirconium carboxylates can be substituted, in whole or in part, as catalysts.

Titanium chelates are formed by reacting a titanium compound with a polyfunctional molecule including polyols such as glycols or glycerine and amino alcohols, amino acids, hydroxy acids, and polycarboxylic acids. Typical chelated esters which serve as catalysts include tetraethylene glycol titanate, tetrapropylene glycol titanate, tetrabutylene glycol titanate, tetra-octylene glycol titanate and tetrapolyethylene glycol titanate, dibutoxy di-(ethylene glycol) titanate, di-isopropoxy di-(octylene glycol) titanates, dimethoxy di-(octylene glycol) titanates, diethyoxy di-(octylene glycol) titanates, tetratriethanol amine titanate, tetratriethanol amine-N-oleate titanate, triethanol amine-N-stearate titanate, triethanol amine-N-linseed acid salt titanate, dibutoxy titanate, dipropoxy titanate, dimethoxy titanate, diethoxy titanate, other dialkoxy dipropoxy, dimethoxy, diethoxy titanates, other dialkoxy di-(amino alcohol) titanates and mixtures thereof The corresponding tin and zirconium chelates can be useful as catalysts.

Preferably, the esterification catalyst is an organometallic catalyst, preferably a titanium, tin, or zirconium organometallic catalyst. More preferably, the esterification catalyst is a titanium alkoxide, titanium carboxylate, or titanium chelate catalyst. More preferably, the catalyst is a titanium alkoxide catalyst.

Preferred carbonyl-like compounds, as defined herein, used as reactant feed to the present invention include carboxylic acids. Carboxylic acids which undergo esterification (i.e., mono or poly-basic acids, preferably dibasic or tribasic acids) can be aliphatic, cyclo-aliphatic or aromatic, they can be substituted or unsubstituted, saturated or unsaturated, or they can be blends of acids. Representative acids include acetic, hydroxyacetic, chloroacetic, bromoacetic, cyanoacetic, 5-phenylacetic, triphenyl acetic, propionic, halopropionic, lactic, beta-hydroxy propionic, n-butyric, isobutyric, n-valeric, isovaleric, 5-phenyl-n-valeric, n-heptanoic, caproic, pelargonic, caprylic, lauric, palmitic, lignoceric, alpha-hydroxy lignoceric, malonic, succinic, glutaric, adipic, pimelic, azelaic, sebacic, decane-1,10-dicarboxylic, pentadecane-1,15-dicarboxylic, pentacosane-1,25-dicarboxylic, 1,2,3-propane tricarboxylic, citric, acrylic, alpha-chloro acrylic, beta-chloro acrylic, beta-bromo acrylic, beta-phenyl acrylic, methacrylic, vinyl acetic, crotonic, angelic, tiglic, undecylenic, oleic, erucic, linoleic, linolenic, maleic, fumaric, mesaconic, citraconic, itaconic, mucconic, aconitic, myristic, stearic, isostearic, branched $C_5$ and $C_{10}$ (e.g., 3,5,5-trimethylhexanoic), branched $C_{17}$, $C_{19}$, $C_{21}$, etc., acids, and mixtures thereof.

Among the alicyclic acids are cyclopropane carboxylic, cyclobutane carboxylic, cyclopentane carboxylic, cycloheptane carboxylic, cyclohexane carboxylic, 2-hydroxy cyclohexane carboxylic, 1,1-cyclopropane dicarboxylic, 1,2-cyclobutane dicarboxylic, 1,3-cyclobutane dicarboxylic, 1,4-cyclohexane dicarboxylic, cyclohexane-1,2,3,4,5,6-hexacarboxylic, cyclopentene-2-carboxylic, 1-cyclohexene-1-carboxylic, hydrocapric, cyclohexadiene-1,2-dicarboxylic, 1,3-cyclohexadiene-1,4-dicarboxylic, and mixtures thereof.

The aromatic acids include benzoic, o-, m- and p-chloro and bromo benzoic, o-, m- and p-hydroxy benzoic, o-, m- and p-nitrobenzoic, o-, m- and p-methoxy benzoic, alpha-napthoic, beta-naphthoic, o-, m- and p-methyl benzoic, o-, m- and p-ethyl benzoic, p-phenyl benzoic, phthalic (1,2-benzene-dicarboxylate), isophthalic, terephthalic, hydroxy phthalic, 2,3-dimethyl benzoic, benzene-1,2,4-tricarboxylic, benzene-1,3,5-tricarboxylic, benzene-1,2,4,5-tetracarboxylic, diacids of naphthalenes and trimellitic, and mixtures thereof. Aromatic acids are currently preferred for plasticizer ester production. Prefereably, the plasticizer acid is phthalic acid (1,2-benzene-dicarboxylate).

When polyols are used to form an ester the following acids are preferred: neopentanoic acid, neoheptanoic, neooctanoic acid, neononanoic acid, neodecanoic acid, 2-ethyl hexanoic acid, oxo-heptanoic acid (i.e., a mix of isomers derived from oxonation/oxidation of hexenes), oxo-decanoic acid (i.e., a mix of isomers derived from oxonation/oxidation of mixed nonenes), oxo-octanoic acid (i.e., a mix of isomers derived from oxonation/oxidation of mixed heptenes), 3,5,5-trimethylhexanoic acid, linear $C_5$–$C_{18}$ alkanoic acids, and mixtures thereof Anhydrides of mono- and poly-basic acids can be used in place of the acids, especially when plasticizer esters are being formed, which is currently preferred. These include acetic anhydride, propionic anhydride, n-butyric anhydride, succinic anhydride, glutaric anhydride, adipic anhydride, pimellic anhydride, maleic anhydride, mesaconic anhydride, citraconic anhydride, glutaconic anhydride, itaconic anhydride, phthalic anhydride, benzoic anhydride, nadic anhydride, methyl nadic anhydride, hexahydrophthalic anhydride, trimellitic anhydride and mixed anhydrides of monobasic acids. Another anhydride is pyromellitic dianhydride. Phthalic anhydride is currently a preferred anhydride.

Among the alcohols which can be reacted with acids and anhydrides are, by way of example, most primary and secondary $C_1$–$_{30}$ monohydric or polyhydric, substituted or unsubstituted alkanols and alkenols, such as, methanol, ethanol, chloroethanol, cyanoethanol, ethoxyethanol, phenylethanol, n-propanol, 2-chloropropanol-1, 3-bromo-propanol-1, 2,2-dichloropropanol-1, isopropanol, propanol-2, 2-nitrobutanol-1, 2-nitrobutanol-1, 2-methylpentanol-1, 2-methyl pentanol-3, the primary and secondary octanols, n-dodecanol, 6-dodecnol, lauryl, myristyl, stearyl, 2-propenol-1, 2-butenol-1, 3-pentenol-1, ethylene glycol, trimethylene glycol, tetramethylene glycol, pentamethylene glycol, glycerol, 1,4-butanediol, decane-1,10-diol, pentadecane-1,15-diol, pentacosane-1,25-diol, 2,4-hexadiene-1,6-diol, 2,4-octadiene-1,8-diol, and aromatic alcohols such as benzyl alcohol, o-, m- and p-methoxy alcohol, o-, m- and p-nitrobenzyl alcohol, o-, m- and p-methyl benzyl alcohol, phenyl ethyl alcohol, triphenyl ethyl alcohol, o-, m- and p-benzyl benzyl alcohol, alpha-naphthyl-ethyl alcohol, beta-naphthyl ethyl alcohol, naphthylene-1,2-diethyl alcohol, phenylene-1,3,5-triethyl alcohol, phenylene-1,4-dioctyl alcohols, and mixtures thereof. This includes higher Guerbet alcohols which are beta carbon branched dimer alcohols having ten to twenty-six carbon atoms.

Polyol (i.e., polyhydroxy) compounds are represented by the general formula:

$R(OH)_{[n]}$ wherein R is an alkyl, alkenyl, or aralkyl hydrocarbyl group and n is at least 2, and can be used in place of the mono alcohols when polyol esters are desired. The hydrocarbyl group may contain from about 2 to 20 or more carbon atoms, and the hydrocarbyl group may also contain substituents such as chlorine, nitrogen, and/or oxygen atoms. The polyhydroxy compounds generally will contain from about 2 to 10 hydroxy groups and more preferably from about 2 to 6 hydroxy groups. The polyhydroxy compound may contain one or more oxyalkylene groups and, thus, the polyhydroxy compounds include compounds such as polyetherpolyols. The number of carbon atoms and number of hydroxy groups contained in the polyhydroxy compound used to form the carboxylic esters may vary over a wide range.

The following alcohols are particularly useful as polyols: neopentyl glycol, 2,2-dimethylol butane, trimethylol ethane, trimethylol propane, trimethylol butane, mono and technical grade (i.e., 88% mono, 10% di and 1–2% tri) pentaerythritol, dipentaerythritol, ethylene glycol, propylene glycol and polyalkylene glycols (e.g., polyethylene glycols, polypropylene glycols, polybutylene glycols, etc., and blends thereof such as a polymerized mixture of ethylene glycol and propylene glycol).

The method according to the present invention is capable of forming plasticizer esters, such as, phthalates, adipates, and trimellitates, from $C_4$–$C_{15}$ alcohols, preferably $C_6$–$C_{13}$ oxo-alcohols. Because of the increase in the rate of reaction, in accordance with this invention, the process is particularly useful in esterifications catalyzed by titanium, zirconium, or tin organometallic catalysts.

This method is also useful in forming polyol esters, such as, neopolyol esters, from polyols and excess fatty acids. The polyol or polyol mixture is preferably technical grade pentaerythritol (PE), trimethyolpropane (TMP), and neopentylglycol, each of which can be admixed with mono-pentaerythritol and/or trimethylol propane or other neopolyols. The preferred acid component is typically a mixture of straight chain acids having five to ten carbon atoms, or a branched chain acid having from five to eighteen carbon atoms, preferably five to nine carbon atoms, namely 2-methylhexanoic, 2-ethylpentanoic, 3,5,5-trimethylhexanoic acids or mixtures thereof. Generally, the acids are monocarboxylic acids. Suitable straight chain acids include, but are not limited to, valeric acid ($C_5$), enanthic acid ($C_7$), caprylic acid ($C_8$), pelargonic acid ($C_9$), and capric acid ($C_{10}$).

The branched chain acid may be iso-$C_5$, iso-$C_7$, iso-$C_8$, or iso-$C_9$. Preferably, the branched chain acid used is the iso-$C_7$ acid. Another preferred branched acid is 3,5,5-trimethylhexanoic acid derived from the oxonation/oxidation of di-isobutylene. Still another preferred branched acid is oxo-octanoic acid derived from the oxonation/oxidation of mixed heptenes.

In the reaction used to form polyol esters, the acid mixture is present in an excess of about 10 to 50 mole percent or more for the amount of polyol used. The excess acid is used to force the reaction to completion. The composition of the feed acid is adjusted so as to provide the desired composition of product ester. After the reaction is complete, the excess acid is removed by stripping and additional finishing.

EXAMPLES

The examples contained herein teach the esterification of phthalic anhydride (PAN) to di-alkyl phthalate. However, the method is equally applicable to the production of adipates, trimellitates, polyol esters, high-hydroxy esters, and other esters formed by the reaction of an acid or anhydride entity with an alcohol utilizing an organometallic catalyst to acheive ultra-high conversion. Each included example used the following protocol. A 20% molar excess of alcohol (to PAN) was charged to a well stirred, 1 liter, 3 neck flask at atmospheric pressure. PAN was added after the system reached a target temperature. A titanium tetra-isopropoxide (Ti(O-iPr)$_4$) catalyst was added as noted in the following tables. The reaction mixture was then heated to about 200° C. and held at 200° C. with nearly constant heat input. The reaction temperature was then maintained at 220° C. with constant boil-up of the mixture provided by control of the pressure in the vessel. The operating pressure started at atmospheric pressure and was slowly reduced throughout the run to approximately 250 mm Hg of vacuum (68.0 kPa) in order to maintain boiling as the water is drawn off and thus the boiling temperature approaches that of the alcohol and ester. Alcohol and water vapor were condensed and separated in a Dean-Stark trap. The water was decanted and the alcohol was returned to the reactor. Tables 1–3 contain data on an alcohol feed which contained 30–60 ppm of cation species with a net positive charge of one. Table 4 contains data obtained from an alcohol feed, which was essentially free of cationic species.

TABLE 1

Staged Catalyst Addition at a Total of 0.40 wt % catalyst on PAN

| | First Stage Catalyst Addition | | | | Second Stage Catalyst Addition | | | | Batch |
|---|---|---|---|---|---|---|---|---|---|
| | Time of cat. add.[1] | % of total cat. | Temp. cat. add. (C) | Water (ppm) | Time of cat. add.[1] | % of total cat. | Temp. cat add. (C) | Water (ppm) | Time (99.9% con.)[2] |
| Base 1 | 0.17 | 100 | 182 | 4000 | n/a | n/a | n/a | n/a | 1.00 |
| Ex. 1 | 0.17 | 50 | 180 | 3100 | 0.25 | 50 | 220 | 1000 | 0.96 |
| Ex. 2 | 0.17 | 50 | 180 | 4000 | 0.25 | 50 | 220 | 1000 | 0.93 |
| Ex. 3 | 0.25 | 50 | 220 | 875 | 0.66 | 50 | 220 | 525 | 0.90 |
| Ex. 4 | 0.25 | 50 | 220 | 1000 | 0.74 | 50 | 220 | 450 | 0.91 |

Examples 1–4 demonstrate that adding a set amount of catalyst in two stages decreases the batch time, at constant conversion, as compared to an equal amount of catalyst added in one initial stage. Examples 1 and 2 demonstrate a beneficial effect of staged catalyst addition (reduced batch time for equal conversion) when the first catalyst addition occurs at water concentrations in excess of 3000 ppm.

Examples 3 and 4 demonstrate increased benefits, in the form of shorter batch times at constant concentration, over examples 1 and 2 gained when the second catalyst charge is added at a water concentration of 1000 ppm or less and the first catalyst addition occurs at water concentrations below 1000 ppm.

TABLE 2

Staged Catalyst Addition at a Total of 0.27 wt % Catalyst on PAN

| | First Stage Catalyst Addition | | | | Second Stage Catalyst Addition | | | | Batch |
|---|---|---|---|---|---|---|---|---|---|
| | Time of cat. add.[1] | % of total cat. | Temp. cat. add. (C) | Water (ppm) | Time of cat. add.[1] | % of total cat. | Temp. cat add. (C) | Water (ppm) | Time (99.9% con.)[2] |
| Base 2 | 0.18 | 100 | 180 | 4000 | n/a | n/a | n/a | n/a | 1.00 |
| Ex. 5 | 0.18 | 48 | 183 | 4100 | 0.38 | 52 | 220 | 1250 | 0.96 |
| Ex. 6 | 0.18 | 75 | 181 | 3500 | 0.38 | 25 | 220 | 1500 | 0.98 |
| Ex. 7 | 0.18 | 75 | 180 | 4000 | 0.38 | 25 | 220 | 1100 | 0.97 |

Examples 5–7 demonstrate that adding a set amount of catalyst in two stages decreases the batch time, at constant conversion, over that obtained in a one stage catalyst addition. Adding a larger percentage of the total catalyst in the first stage, while still beneficial over a one stage catalyst addition, is less beneficial then adding about equal catalyst amounts in both stages.

TABLE 3

Staged Catalyst Addition at a Total of 0.54 wt % Catalyst on PAN

| | First Stage Catalyst Addition | | | | Second Stage Catalyst Addition | | | | Batch |
|---|---|---|---|---|---|---|---|---|---|
| | Time of cat. add.[1] | % of total cat. | Temp. cat. add. (C) | Water (ppm) | Time of cat. add.[1] | % of total cat. | Temp. cat add. (C) | Water (ppm) | Time (99.9% con.)[2] |
| Base 3 | 0.19 | 100 | 180 | 2300 | n/a | n/a | n/a | n/a | 1.00 |
| Ex. 8 | 0.19 | 50 | 182 | 3800 | 0.39 | 50 | 220 | 1300 | 0.98 |

TABLE 4

Staged Catalyst Addition at a Total of
.27 wt % Catalyst on PAN - Low Cation Feed

|  | First Stage Catalyst Addition | | | | Second Stage Catalyst Addition | | | | Batch |
| --- | --- | --- | --- | --- | --- | --- | --- | --- | --- |
|  | Time of cat. add.[1] | % of total cat. | Temp. cat. add. (C) | Water (ppm) | Time of cat. add.[1] | % of total cat. | Temp. cat add. (C) | Water (ppm) | Time (99.9% con.)[2] |
| Base 4 | 0.2 | 100 | 180 | 4000 | n/a | n/a | n/a | n/a | 1.00 |
| Ex. 9 | 0.2 | 50 | 180 | 4100 | 0.44 | 50 | 220 | 1000 | 0.97 |
| Ex. 10 | 0.2 | 50 | 180 | 4250 | 0.35 | 50 | 220 | 1250 | 0.98 |

Notes (all tables):
1. Fraction of the base case total batch time.
2. Normalized to the batch time for the base case (single stage catalyst addition).
3. The following relationships between the four tables is provided to accommodate comparison between data points appearing in different tables:
The batch time ratio of Base 2:Base 1 = 1.25;
The batch time ratio of Base 3:Base 1 = 1.03;
The batch time ratio of Base 4:Base 1 = 0.90.

Examples 9 and 10 demonstrate that staged catalyst addition is also effective in reducing reaction batch times for a reaction mixture that does not contain appreciable cation species.

While several embodiments in accordance with the invention are shown and described, one skilled in the art will understand that the same are susceptible to numerous changes. Therefore, the present invention is not limited to the details shown and described, but is intended to encompass all changes and modifications which come within the scope of the appended claims.

We claim:

1. A process for the production of an ester, comprising:
   (a) reacting an alcohol with a carbonyl-like compound in the presence of a first amount of a first esterification catalyst to form a reaction mixture; and
   (b) adding a second amount of a second esterification catalyst to said reaction mixture at some time after initiation of step (a), wherein said second esterification catalyst is the same or different from said first esterification catalyst.

2. A process as claimed in claim 1, wherein said carbonyl-like compound is a carboxylic acid, an anhydride, or combinations thereof.

3. A process as claimed in claim 2, wherein said first esterification catalyst and said second esterification catalyst are tin organometallic catalysts, zirconium organometallic catalysts, or titanium organometallic catalysts.

4. A process as claimed in claim 3, wherein step (b) is initiated after the water content of said reaction mixture, not including the weight of catalyst, is less than 5,000 ppm.

5. A process as claimed in claim 4, wherein step (b) is initiated after the water content of said reaction mixture, not including the weight of catalyst, is less than 1000 ppm.

6. A process as claimed in claim 4, wherein the total of said first amount of said first esterification catalyst and said second amount of said second esterification catalyst is from about 0.01 to 1.0 weight % of said carbonyl-like compound used in step (a).

7. A process as claimed in claim 6, wherein the total of said first amount of said first esterification catalyst and said second amount of said second esterification catalyst is from about 0.1 to 0.45 weight % of said carbonyl-like compound used in step (a).

8. A process as claimed in claim 4, wherein said first amount of said first esterification catalyst is contacted with said alcohol and said carbonyl-like compound at a temperature from about 170° C. to 230° C.

9. A process as claimed in claim 4, wherein said first amount of said first esterification catalyst is from about 5 to 80 weight % of the total of said first amount of said first esterification catalyst and said second amount of said second esterification catalyst.

10. A process as claimed in claim 9, wherein said first amount of said first esterification catalyst is from about 15 to 60 weight % of the total of said first amount of said first esterification catalyst and said second amount of said second esterification catalyst.

11. A process as claimed in claim 4, wherein said carbonyl-like compound is phthalic anhydride or 1,2-benzene-dicarboxylate.

12. A process as claimed in claim 4, wherein said first esterification catalyst and said second esterification catalyst are titanium alkoxide catalysts, titanium carboxylate catalysts, or titanium chelate catalysts.

13. A process as claimed in claim 12, wherein said first esterification catalyst and said second esterification catalyst are the same.

14. A process as claimed in claim 4, wherein said alcohol is an alcohol containing 6, 7, 8, 9, 10, 11, 12, or 13 carbon atoms.

15. A process as claimed in claim 4, wherein said alcohol contains two or more hydroxyl groups.

16. A process for the production of an ester, comprising:
   (a) reacting an alcohol with a carbonyl-like compound in the presence of a first amount of a first esterification catalyst to form a reaction mixture, wherein said reaction mixture contains a cation species; and
   (b) adding a second amount of a second esterification catalyst to said reaction mixture at some time after initiation of step (a), wherein said second esterification catalyst is the same or different from said first esterification catalyst.

17. A process as claimed in claim 16, wherein said cation species has a net positive charge of $^{+}1$.

18. A process as claimed in claim 17, wherein said cation species is $Li^{+1}$, $Na^{+1}$, $K^{+1}$, $Cu^{+1}$, $Rb^{+1}$, $Ag^{+1}$, $Cs^{+1}$, or $Au^{+1}$.

19. A process as claimed in claim 18, wherein said carbonyl-like compound is a carboxylic acid, an anhydride, or combinations thereof.

20. A process as claimed in claim 19, wherein said first esterification catalyst and said second esterification catalyst are tin organometallic catalysts, zirconium organometallic catalysts, or titanium organometallic catalysts.

21. A process as claimed in claim 20, wherein step (b) is initiated after the water content of said reaction mixture, not including the weight of catalyst, is less than 5,000 ppm.

22. A process as claimed in claim 21, wherein step (b) is initiated after the water content of said reaction mixture, not including the weight of catalyst, is less than 1000 ppm.

23. A process as claimed in claim 21, wherein the total of said first amount of said first esterification catalyst and said second amount of said second esterification catalyst is from about 0.01 to 1.0 weight % of said carbonyl-like compound used in step (a).

24. A process as claimed in claim 23, wherein the total of said first amount of said first esterification catalyst and said second amount of said second esterification catalyst is from about 0.2 to 0.5 weight % of said carbonyl-like compound used in step (a).

25. A process as claimed in claim 21, wherein said first amount of said first esterification catalyst is contacted with said alcohol and said carbonyl-like compound at a temperature from about 170° C. to 230° C.

26. A process as claimed in claim 23, wherein said first amount of said first esterification catalyst is from about 5 to 80 weight % of the total of said first amount of said first esterification catalyst and said second amount of said second esterification catalyst.

27. A process as claimed in claim 24, wherein said first amount of said first esterification catalyst is from about 15 to 60 weight % of the total of said first amount of said first esterification catalyst and said second amount of said second esterification catalyst.

28. A process as claimed in claim 21, wherein said carbonyl-like compound is phthalic anhydride or 1,2-benzene-dicarboxylate.

29. A process as claimed in claim 21, wherein said first esterification catalyst and said second esterification catalyst are titanium alkoxide catalysts, titanium carboxylate catalysts, or titanium chelate catalysts.

30. A process as claimed in claim 29, wherein said first esterification catalyst and said second esterification catalyst are a titanium alkoxide catalyst.

31. A process as claimed in claim 21, wherein said alcohol is an alcohol containing 6, 7, 8, 9, 10, 11, 12, or 13 carbon atoms.

32. A process for the production of an ester, comprising:
(a) reacting an alcohol with a carbonyl-like compound in the presence of a first amount of a first esterification catalyst in a first reaction zone to form a first reaction product; and
(b) reacting at least a portion of said first reaction product with a second amount of a second esterification catalyst in a second reaction zone to form a second reaction product, wherein said second esterification catalyst is the same or different from said first esterification catalyst.

33. A process as claimed in claim 32, wherein said process is a continuous process.

34. A process as claimed in claim 33, wherein said carbonyl-like compound is a carboxylic acid, an anhydride, or combinations thereof.

35. A process as claimed in claim 34, wherein said first esterification catalyst and said second esterification catalyst are tin organometallic catalysts, zirconium organometallic catalysts, or titanium organometallic catalysts.

36. A process as claimed in claim 35, wherein said first esterification catalyst and said second esterification catalyst are titanium alkoxide catalysts, titanium carboxylate catalysts, or titanium chelate catalysts.

37. A process as claimed in claim 35, wherein the total of said first amount of said first esterification catalyst and said second amount of said second esterification catalyst is from about 0.01 to 1.0 weight % of said carbonyl-like compound used in step (a).

38. A process as claimed in claim 35, wherein said first amount of said first esterification catalyst is contacted with said alcohol and said carbonyl-like compound at a temperature from about 160° C. to 250° C.

39. A process as claimed in claim 35, wherein said first amount of said first esterification catalyst is from about 5 to 80 weight % of the total of said first amount of said first esterification catalyst and said second amount of said second esterification catalyst.

40. A process as claimed in claim 35, wherein said carbonyl-like compound is phthalic anhydride or 1,2-benzene-dicarboxylate.

41. A process as claimed in claim 35, wherein said alcohol is an alcohol containing 6, 7, 8, 9, 10, 11, 12, or 13 carbon atoms.

42. A process as claimed in claim 34, further comprising:
(c) reacting at least a portion of said second reaction product with a third amount of a third esterification catalyst in a third reaction zone to form a third reaction product.

* * * * *